United States Patent [19]

Keldahl et al.

[11] Patent Number: 4,846,818
[45] Date of Patent: Jul. 11, 1989

[54] INCONTINENCE APPLIANCE

[75] Inventors: Loren R. Keldahl, Edina; Dale C. Lindquist, Willmar, both of Minn.

[73] Assignee: Conceptus, Inc., Willmar, Minn.

[21] Appl. No.: 194,849

[22] Filed: May 17, 1988

[51] Int. Cl.⁴ .............................................. A61F 5/44
[52] U.S. Cl. .................................. 604/329; 128/761; 600/30; 604/330
[58] Field of Search ........................ 604/317, 327–332, 604/354; 128/DIG. 25, 760, 761, 767, 887; 600/29–32; 623/12, 14, 66

[56] References Cited

U.S. PATENT DOCUMENTS

| | | | |
|---|---|---|---|
| 3,116,734 | 1/1964 | Terman | 604/329 |
| 3,565,073 | 2/1971 | Giesy | 128/283 |
| 3,646,616 | 3/1972 | Keshin | 3/1 |
| 3,661,155 | 5/1972 | Lindan | 604/329 |
| 3,939,821 | 2/1976 | Roth | 128/DIG. 25 |
| 3,952,726 | 4/1976 | Hennig et al. | 128/DIG. 25 |
| 4,198,979 | 4/1980 | Cooney et al. | 128/295 |
| 4,205,678 | 6/1980 | Adair | 128/283 |
| 4,258,705 | 3/1981 | Sorensen et al. | 600/30 |
| 4,484,917 | 11/1984 | Blackmon | 604/327 |
| 4,568,339 | 2/1986 | Steer | 604/329 |
| 4,631,061 | 12/1986 | Martin | 604/318 |
| 4,676,802 | 6/1987 | Tofield et al. | 623/66 |
| 4,690,677 | 9/1987 | Erb | 604/327 |

Primary Examiner—Stephen C. Pellegrino
Assistant Examiner—Mario Costantino
Attorney, Agent, or Firm—Kinney & Lange

[57] ABSTRACT

A device for alleviating problems associated with urinary incontinence in female patients that has an external, magnetically retained, elastically expandable receptacle which includes a rim that can be formed to fit between the labia of a female circumscribing the urthra outlet with a rear portion inserted in the vagina using magnetically attractable elements implanted at the foward portion of the labia. The set of implanted elments mate with a set of elements mounted on the receptacle rim and the sets of elements are magnetically attractable to each other. Suitable sealing jels can be used around the edges of the rim. The receptacle includes an anterior collection cylinder, which is folded when empty and which is sufficiently expandable so that it will unfold and hold voided volumes adequately to permit rapid voiding without causing pressures that break the seals of the rim. The collection cylinder can be drained when convenient.

18 Claims, 3 Drawing Sheets

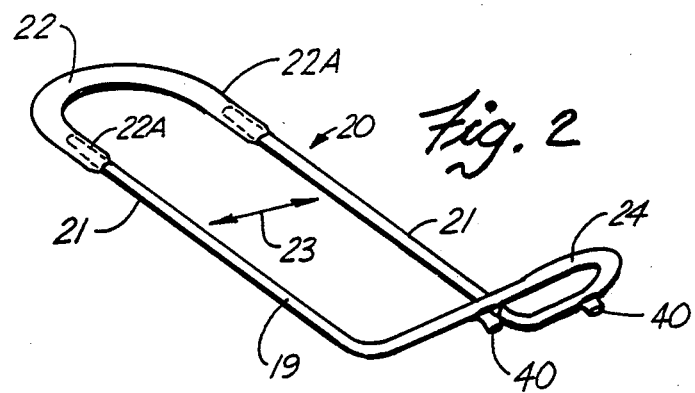
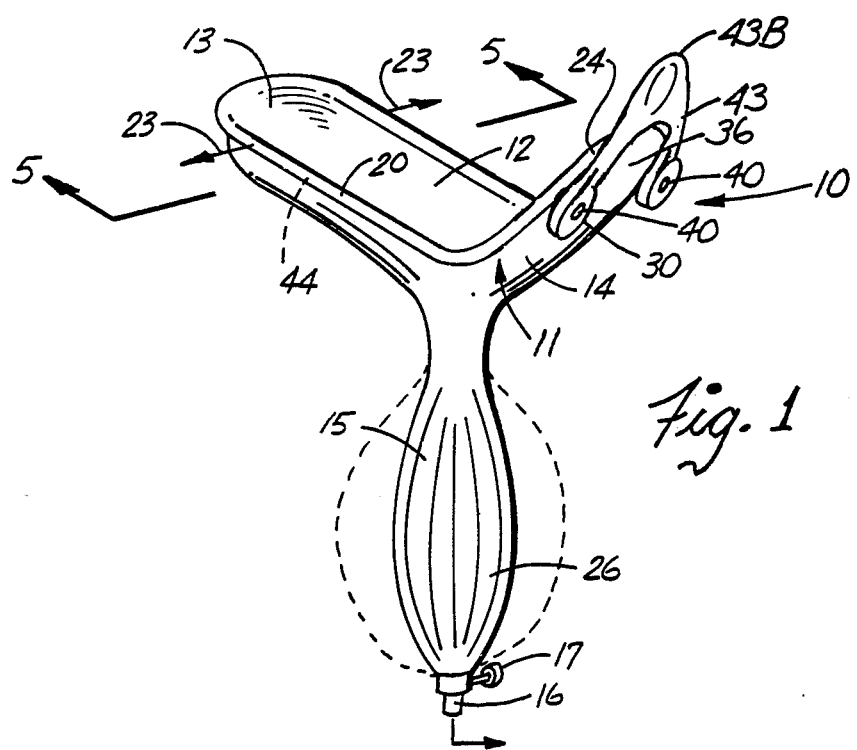

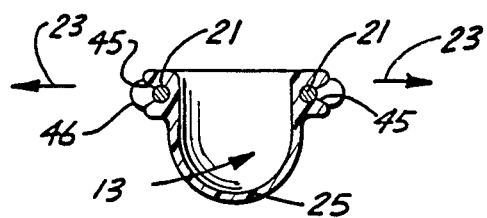
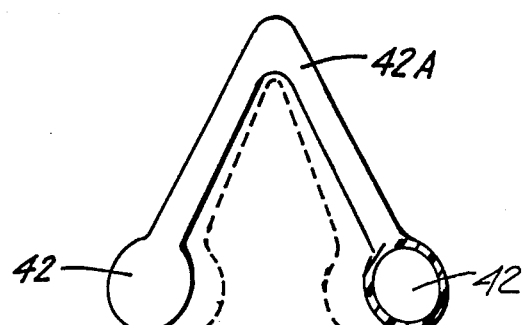
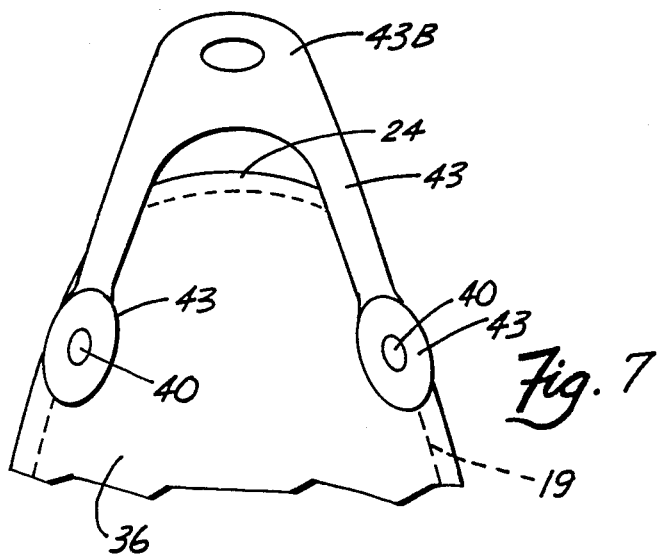
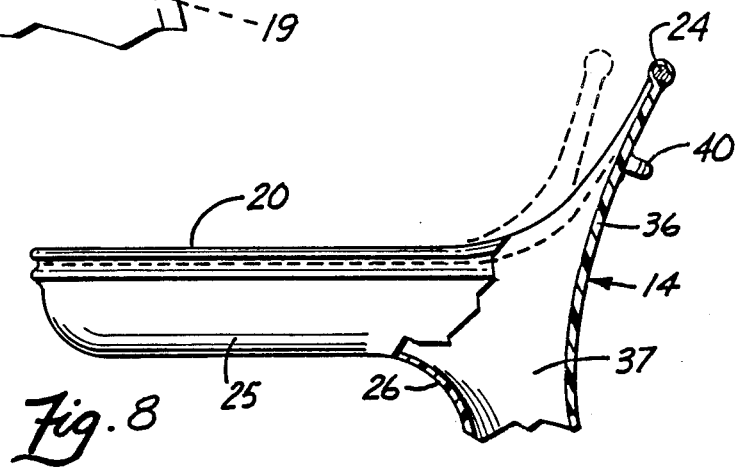

INCONTINENCE APPLIANCE

BACKGROUND OF THE INVENTION

1. Field of the Invention

The present invention relates to long term incontinence appliances for females.

2. Description of the Prior Art

Various collecting members have been utilized for exterior collection of human waste. In cases of colostomy, illeostomy, or ureterostomy urostomy, an exterior opening is created through the abdomen wall, and U.S. Pat. No. 3,565,073 shows a backing element that is implanted beneath the skin, and an external element carried on a bag with one of the elements being a magnet and the other element either another magnet or a magnetic material to provide for holding a waste collection bag in place.

A similar ostomy bag retainer is disclosed in U.S. Pat. No. 4,205,678.

Additional efforts to provide collection devices for accomodating incontinence have been advanced, and the present device shows an easily secured, easily shaped, and reliable collection appliance that is primarily mounted to minimize any opportunity for external detection in normal functions.

SUMMARY OF THE INVENTION

The present invention relates to an incontinence appliance that is held in place between the labia in the vulvar orifice of a female to hold a collecting appliance of flexible material below the orifice from the urethra, and which is retained in place and sealed to minimize leakage. The appliance is fixed in position by magnetic attraction between two magnetically attractable elements, one of which is implanted beneath the mucousal surface of the anterior portion of the labia and the other of which is carried by the collecting appliance.

The appliance includes an inner end canal portion which fits into the vagina and a forward end that fits over the urethra orifice and extends forwardly. The retaining elements are mounted on the forward end of the appliance.

The appliance has a rim which is formed from a malleable rod that defines sides and forward edges of an open top chamber defined in the collecting appliance. The base or inner end of the rim is spring-loaded to provide outward stabilizing force on the side edges. The malleable rod can be manually shaped to conform to individual anatomical variations. The edges will provide an adequate surface for applying a sealant that seals the rim edges on adjacent surfaces. The spring load or bias will urge the side edges outwardly to engage the wall of the vagina. The anterior or front magnetic members will retain the appliance seated in proper position during normal activities.

The appliance is easily manufactured from non-toxic elastomers. The malleable rod is made of known materials, such as the type of material utilized in penile implants. The malleable rod may be made of suitable non-magnetic metals, or suitable elastomers. Generally, a composite rod of two different types of elastomers can be used.

The spring member at the inner end of the rim, as stated, provides an outwardly spring load on the side rod portions. The spring can be a "U"-shaped elastomer that has legs which embed opposite ends of the malleable rod. The rod portion extends to form the sides of the rim. The spring can be some other type of material that will provide a biasing force outwardly on the side rod portions to tend to maintain a seal with the adjacent surfaces along the sides of the rim.

The appliance is retained in place by the magnetic members near the front of the vulvar orifice. The submucousal, implanted magnets (or members of magnetically permeable material) are urged to hold the elements carried by the appliance rim to resist movement of the appliance from forces that are generated by voiding the bladder. The rim remains sealed along the sides and is held securely.

The appliance preferably has a forward end portion that is a molded, thin flexible elastomer material collector cylinder that can be pleated when formed and which will open or unfold if a sudden volume is expelled, to insure that the back pressures created at the outlet will not increase to cause retrograde flow in the appliance so that the rim is forced out of position to cause leaks to occur.

The rim is made of sufficient fore and aft length so that it extends rearwardly into the vagina. Thus, a fairly large open top chamber is provided in the appliance and it is securely held in place with the magnetic attraction means. The appliance can be removed for cleaning, disinfecting or sterilizing and easily replaced.

BRIEF DESCRIPTION OF THE DRAWINGS

FIG. 1 is a perspective view of an incontinence appliance made according to the present invention;

FIG. 2 is a perspective view of a rim member used with the appliance of the present invention;

FIG. 5 is a sectional view taken on line 5—5 in FIG. 1;

FIG. 6 is a plan view of an implantable magnet assembly used with the present invention;

FIG. 7 is a plan view of replaceable magnetic members used on the appliance of the present invention; and FIG. 8 is a fragmentary side view of the appliance of the present invention with parts in section and parts broken away.

DETAILED DESCRIPTION OF THE PREFERRED EMBODIMENTS

Figure 3:
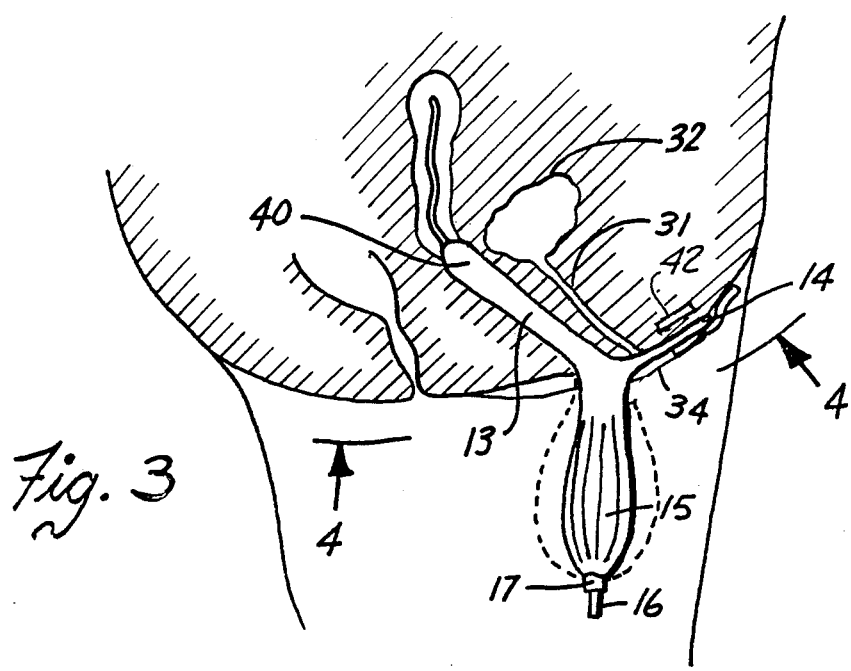
FIG. 3 is a schematic body sectional view showing the incontinence appliance in place on a female wearer.

In FIG. 1, the incontinence appliance indicated generally at 10 comprises a chamber forming, elastomeric open top receptacle member 11, that has an open top upper portion 12 that forms an inlet. The upper portion 12 is elongated in a fore and aft direction and the receptacle includes a canal portion 13 of size so it will fit into a vagina. The receptacle member 11 includes a forward portion 14 that has a collector cylinder 15 depending therefrom. The collector cylinder 15 is elastomeric and has a pleated wall and is shaped as shown in FIGS. 1 and 3. The lower end of the collector cylinder tapers toward an outlet neck 16. Neck 16 has an internal passageway that includes a valve 17 of suitable design which can be closed to retain urine in the collector cylinder. The neck can be connected to a leg bag or other container of conventional design. When the valve 17 is opened, urine will be discharged from the collector cylinder. The pleating permits rapid filling (expansion) without back pressure caused by neck 16 and the cylinder 15 expels the liquid as the pleats return to their normal position.

The receptacle member 11 has an upper rim member 20 that defines the mouth or opening to the canal portion 13 and to the collector cylinder. The rim member 20 comprises a malleable rod 19 forming two elongated longitudinally extending malleable side rod portions 21,21 which are joined at the forward end of the member 11 by a cross over yoke portion 24 of the malleable rod 19 at the front end of forward portion 14. The yoke 24 has side legs that are spaced apart and join the side rod portions. The malleable rod is molded into a suitable non-toxic, non-interactive thin elastomeric material wall 25, such as a silicone material wall, that is preferably also molded to form the walls 26 of the canal portion chamber and the pleated walls of the collector cylinder 15. The collector cylinder 15 is made to unfold to size approximately as shown in dotted lines.

Figure 4:
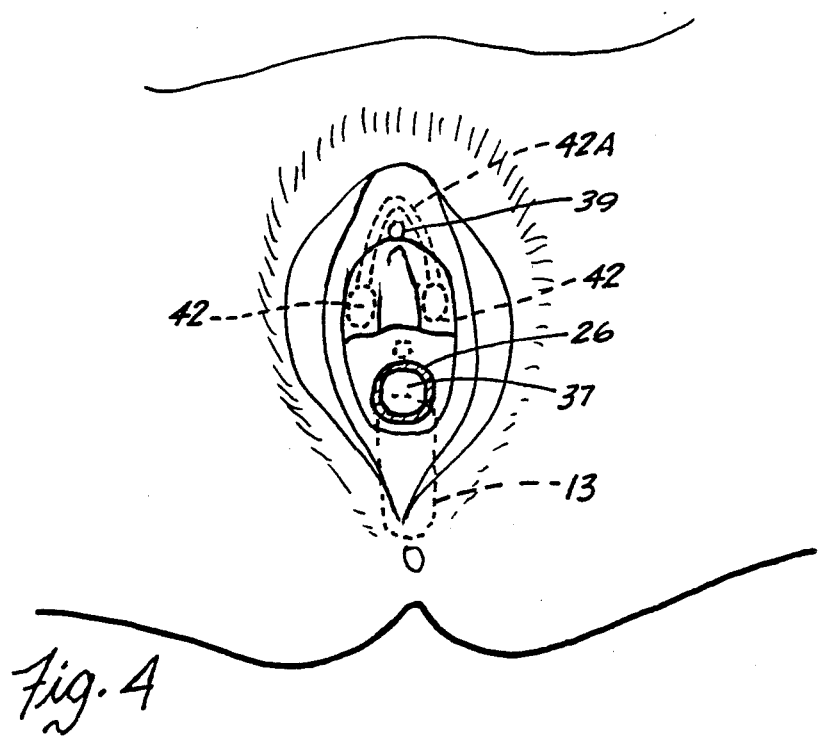
FIG. 4 is a schematic view taken on line 4—4 in FIG. 3 showing the implanted magnets used in place on a female and with the incontinence appliance broken away.

An inner, U-shaped end member 22 of the rim member 20 is made of a spring or resilient material. The ends of the legs 22A of the U-shaped member 22 embed the rod side portions 21, respectively, so the rod is held securely on the spring member 22. When moved into place in the vagina, the spring legs 22A will move inwardly and thus exert an outward pressure as indicated by the arrows 23 in FIGS. 2 and 5, on the rod side portions 21. The malleable rod 19 and rod side portions 21,21 can be bent and formed and will retain the formed shape. The rod 19 can be made to fit so the canal portion will be comfortable when fitted into a human female body indicated generally at 30. The receptacle member 11 is made so the closed end of the canal portion 13 slides into the vagina. The wall 25 forming the canal portion will yield and move for fitting as well. The forward portion 14 extends forwardly of and encompasses the orifice from the urethra, indicated at 31, leading from a bladder 32, and to collect urine that is discharged. The forward portion of the rim 20 that is external of the vagina seats between the labia indicated at 35 in FIG. 4, and seals primarily on the mucosal surface of the labia minora. The front or anterior portion of the flexible wall supported by yoke portion 24 of the rod 19 and shown at 36 deflects urine into the opening 37 of the collector cylinder 15 (see FIGS. 4 and B). The appliance is stabilized by the canal portion 13 and the rim 20 defining the canal portion, which are inserted into and seated in the vagina. The collector cylinder 15 does contract to a size that is sufficiently small for comfort.

As can be seen in FIG. 3, the labia majora indicated at 34 extends downwardly from the rim 20 along the sides of the collector cylinder 15.

At the forward or anterior end 14 of the incontinence appliance 10, the legs of the yoke portion 24 of the rod 19 has support hooks or legs indicated generally at 40,40 extending forwardly therefrom. The forward end of the yoke extends anteriorly beyond the clitoris 39 and the legs of the yoke portion fit around it. The malleable rod 19, including side rod portions 21,21 can be formed so that the support hooks or lugs 40,40 are spaced apart and can be malleable or resilient.

A pair of implanted magnetically attractable elements or members 42,42 are implanted submucously in the labia minora toward the anterior opening of the vulvar orifice on opposite sides of the vestibule. The elements 42 are spaced apart a distance substantially equal to the spacing of the support hooks or lugs 40 as illustrated generally in FIG. 2. The implanted magnetic elements 42 are joined with a wishbone connector or yoke 42A (see FIGS. 4 and 6) for stability and to prevent migration after implanting. The magnetic elements 42 are smoothly shaped for example, elliptical, and can be molded to the yoke 42A, which also can be a molded or malleable material. Of course, the exterior of the yoke and magnetic elements can be coated with a molded, non-toxic material. The yoke can be formed for fitting different anatomies.

A separate magnetic element or member 43 is removably supported on each of the hooks or lugs 40. The magnetic elements 43 are supported on a separate yoke 43A, also shaped as a wishbone which generally matches the yoke 42A. The hooks or lugs 42 fit into openings in the magnetic elements 43 and can frictionally engage the surfaces of the opening for retaining the element 43. Other retainers can be used. A pull tab 43B is formed on the yoke and is external for aid in removal of the appliance.

The magnetic elements 43 are spaced the same distance as the implanted magnetic elements 42. The magnetic elements 43 are external and on the outside of the rod front yoke portion 24.

At least one of the sets of elements 42 and 43 is a permanent (ceramic) magnet, and the other set can be a magnet or a magnetically permeable (attracted) material. The sets of magnetic elements 42 and 43 must be attracted together by magnetic force.

The magnets used must have adequate force to insure that the canal portion 13 remains seated in the vagina and sealed along the rim 20. The force from the magnetic elements keeps the appliance seated during normal activity, such as walking and the magnetic force resists gravity forces and voiding pressures. Some compression of the skin layer between the two aligning and attractable elements 42 and 43 will occur, which contributes to a firm holding and a tight seal. The region of sealing is indicated in dotted lines at 44 in FIGS. 1 and S. As shown in FIG. 5, the rim 20 has a concave channel 45 which insures that an adequate supply of sealing jel 46 is retained on the outside of the canal 13.

The inner surface of the yoke portion 24 of the rim also can have a recess for the sealing jel. Jel is used around the rim where the canal portion 13 exits the vagina to insure an adequate seal. Since the inner end spring 26 of the canal portion 13 provides a biasing outward load on the exterior of the rim, there is effective sealing. The rim seals only on mucousal surfaces and not on the skin.

The collection cylinder 15 of the appliance is flexible and pleated and is folded when in a position as shown in FIG. 3. When subjected to a voiding of the bladder 32, the collection cylinder 15 will expand outwardly as shown in the dotted lines in FIGS. 1 and 3, and will provide a cylinder of volume sufficient to accept a full bladder volume of urine without causing a pressure tending to force the rim 20 away from the sealing position, and to insure the magnetically attractable elements are not separated. The neck 16 and valve 17 form a restriction to flow even if a leg bag is used that is not sufficiently large to permit immediate passage of a sudden voiding.

The specific materials used can be varied, but non-irritant materials are important, as well as long-lasting elastomers. The magnetic elements 42 or 43 can be any strong permanent magnet that will provide sufficient force for holding the appliance in place. Ceramic magnets are presently preferred.

The malleable rod 19 is preferably in the range of 1/16 to ⅛ of an inch in diameter, to keep the size of the rim 20 small. The overall length of the appliance will be in the range of 3–5 inches and the width is in the range of 1 inch. The rod forming the rim can be a continuous, closed loop of metal or synthetic material that is springy at the closed end (with no separate spring member 22) to provide the outward force along the side members represented as malleable rod portions 21.

The magnetic elements 43, and yoke 43A which comprises a set of elements can be reused and replaced on new appliances 10 when the appliance itself, including the rim and flexible walls require replacing. The appliance can be cleaned, sterilized or disinfected and replaced on a routine basis thereby preventing infections and odors. Erosion or wear will eventually require replacement of the appliance. The high cost magnets do not require frequent replacement.

Although the present invention has been described with reference to preferred embodiments, workers skilled in the art will recognize that changes may be made in form and detail without departing from the spirit and scope of the invention.

What is claimed is:

1. An incontinence appliance for female patients comprising an open top receptacle, said receptacle being defined by a rim, and having a forward portion and a rear portion, a flexible wall supported by said rim to form the receptacle and having an outlet portion at a lower end thereof adjacent the forward portion, a first means for securing attached to the forward portion, and at least one second means for securing adapted for implanting into the pubic region of a female wearer of the appliance, at least one of the first and second means being a magnet and at least one or the other of the first and second means being attracted to the magnet, and the rear portion of the receptacle being formed of size to fit at least partially within the vagina of a female wearing the appliance when the magnetically attractable elements are in position, whereby the rim is retained by magnetic attraction and the rim circumscribes an outlet orifice from a urethra of a wearer.

2. The apparatus as specified in claim 1 wherein said rim comprises malleable side rod portions, and an inner end rim portion constructed to exert a separating force on the malleable side rod portions.

3. The apparatus as specified in claim 1 wherein said receptacle includes a collector cylinder at a forward portion comprising a foldable elastomeric material adapted to be initially folded to a first size, and upon being subjected to voiding of a bladder unfolding to provide an internal volume greater than in the folded condition.

4. The apparatus as specified in claim 1 wherein said rim of the receptacle at the forward portion thereof comprises a yoke means which during use is external of a vagina of a wearer and carries a baffle wall forwardly of the opening orifice from a urethra of a wearer, and engages mucousal surfaces at a forward portion of the vulvar orifice of a wearer.

5. The apparatus as specified in claim 1 wherein at least one of said first and second means for securing comprises a permanent magnet.

6. The apparatus of claim 1 wherein the rim has elongated side rod portions extending forwardly from a rear end, and which are joined at the forward portion by a yoke having side legs joining the side rod portions;
the first securing means comprising element mounted on the leg of the yoke, and the second securing means being a separate element for implanting in aligning relationship with each element of the first securing means.

7. The apparatus of claim 6 wherein the elongated side rod portions are joined at a closed inner end of the receptacle by joining means which includes means for providing a spring bias urging the side rod portions to separate to provide a side sealing effect on adjacent surfaces of a vagina in which the rear portions of the appliance are placed.

8. The apparatus of claim 6 wherein the side rod portions comprise manually manipulatable malleable members which can be deformed for sealingly fitting a wearer.

9. The apparatus of claim 6 wherein the elements of the first securing means are removably mounted onto the legs of the yoke.

10. The apparatus of claim 9 and means coupling the elements of the first securing means together and forming an exterior magnet assembly.

11. The apparatus of claim 1 wherein the second means for securing comprises a pair of elements connected to a yoke means shaped to permit implanting the elements submucousally with the yoke means extending on opposite sides of a clitoris of a wearer, with a closed end of the yoke means extending anteriorly of such clitoris when implanted.

12. An incontinence appliance for females comprising a support rim, said support rim defining an opening and having a forward portion and a rear portion, a flexible receptacle attached to and supported by said rim and having an outlet at a lower part of the forward portion thereof, and first means for securing attached to the forward position, and at least one second means for securing adapted for implanting into the body of a female wearer of the appliance, at the anterior portion of a vulvar orifice of such wearer, the first and second means for securing being magnetically attracted to each other, and the rim being of size to fit against exterior mucousal surfaces, circumscribing an outlet orifice from a urethra of a female wearing the appliance when the magnetically attractable means for securing are in position whereby the rim is retained by magnetic attraction.

13. The apparatus as specified in claim 12 wherein said rim comprises malleable side portions and an inner end portion constructed to exert a separating force on the malleable side portions.

14. The apparatus as specified in claim 12 wherein said receptacle comprises a flexible foldable collection cylinder supported by the rim at the forward portion of the rim.

15. The apparatus of claim 14 and an outlet passageway at the lower portion of the collection cylinder, and valve means for controlling flow through the outlet passageway.

16. The apparatus of claim 15 wherein the rear portion of the rim is of size to fit within a vagina of a wearer for support, the forward portion being anterior of the vaginal opening during use.

17. The apparatus of claim 13 wherein the inner end portion comprises a U-shaped member made of spring material and having side legs, the rim side rod portions being supported by the side legs of the U-shaped member, the forward ends of the rim side portion being bent out of the plane of the rim for providing supports for the first means for securing and forming a continuous rim line for sealing around the outlet orifice of a urethra of a wearer.

18. The apparatus of claim 17 and means on the rim for supporting a sealing jel on surfaces engaging the mucousal surfaces of a wearer of the appliance.

* * * * *

UNITED STATES PATENT AND TRADEMARK OFFICE
CERTIFICATE OF CORRECTION

PATENT NO. : 4,846,818

DATED : July 11, 1989

INVENTOR(S) : Loren R. Keldahl

It is certified that error appears in the above-identified patent and that said Letters Patent is hereby corrected as shown below:

Column 5, line 30, after "wall", insert --attached to and--.

Column 6, line 3, delete "element" and insert --elements--.

Signed and Sealed this

Twenty-fourth Day of April, 1990

Attest:

HARRY F. MANBECK, JR.

*Attesting Officer*  *Commissioner of Patents and Trademarks*